(12) United States Patent
Goetz

(10) Patent No.: US 9,072,771 B1
(45) Date of Patent: Jul. 7, 2015

(54) LOCOMOTIVE ANTENNA ARRAYS

(75) Inventor: Christopher John Goetz, Hamburg, NY (US)

(73) Assignee: STI-CO INDUSTRIES, INC., Orchard Park, NY (US)

( * ) Notice: Subject to any disclaimer, the term of this patent is extended or adjusted under 35 U.S.C. 154(b) by 624 days.

(21) Appl. No.: 13/199,339

(22) Filed: Aug. 26, 2011

(51) Int. Cl.
*H01Q 1/32* (2006.01)
*A61K 48/00* (2006.01)
*H01Q 1/28* (2006.01)

(52) U.S. Cl.
CPC *A61K 48/00* (2013.01); *H01Q 1/32* (2013.01); *H01Q 1/28* (2013.01)

(58) Field of Classification Search
USPC .......................... 343/703, 705, 711, 712, 713
See application file for complete search history.

(56) References Cited

U.S. PATENT DOCUMENTS

| | | | |
|---|---|---|---|
| 4,184,160 A * | 1/1980 | Affronti ........................ | 343/712 |
| 4,253,099 A | 2/1981 | Yamazaki et al. | |
| 4,749,997 A | 6/1988 | Canonico | |
| 5,706,015 A * | 1/1998 | Chen et al. ............. | 343/700 MS |
| 6,091,372 A | 7/2000 | Dienes | |
| 6,191,752 B1 | 2/2001 | Lester et al. | |
| 6,618,018 B1 | 9/2003 | Sylvester et al. | |
| 6,990,322 B2 | 1/2006 | Harris et al. | |
| 7,202,827 B2 | 4/2007 | Donald | |
| 7,436,362 B2 | 10/2008 | Noro | |
| 7,557,763 B2 | 7/2009 | Bilyeu et al. | |
| 2003/0214447 A1 * | 11/2003 | Sasagawa et al. ............. | 343/713 |
| 2005/0264461 A1 * | 12/2005 | Sugimoto et al. ............. | 343/713 |
| 2006/0044196 A1 * | 3/2006 | Grant et al. .................... | 343/713 |
| 2007/0013594 A1 * | 1/2007 | Yegin et al. .................... | 343/713 |
| 2007/0040757 A1 * | 2/2007 | Blickle ........................ | 343/713 |
| 2008/0055171 A1 | 3/2008 | Noro et al. | |
| 2009/0051608 A1 | 2/2009 | Johnson et al. | |
| 2009/0207084 A1 | 8/2009 | Ikeda et al. | |
| 2010/0013724 A1 | 1/2010 | Ohshima et al. | |

* cited by examiner

*Primary Examiner* — Tho G Phan
(74) *Attorney, Agent, or Firm* — Kenneth J. Lukacher Law Group

(57) ABSTRACT

An antenna array is provided having multiple antenna elements mountable to the roof of a locomotive. Each of the antenna elements has a separate signal path of one or more conductive elements in a housing and shares a common hole or opening to outside the housing through which the signal path of each antenna element is extendable. The signal path of each antenna element then extends via a common access hole in the roof of the locomotive for enabling one or more of passage of signals to or from the antenna element. The access hole is below the array when the common hole is along the bottom of the housing, and elsewhere along the roof when the common hole is along a side of the housing. Two of the antenna arrays may be mounted in a parallel relationship spaced from each other along the locomotive roof and share the same or a different access hole in such roof.

18 Claims, 11 Drawing Sheets

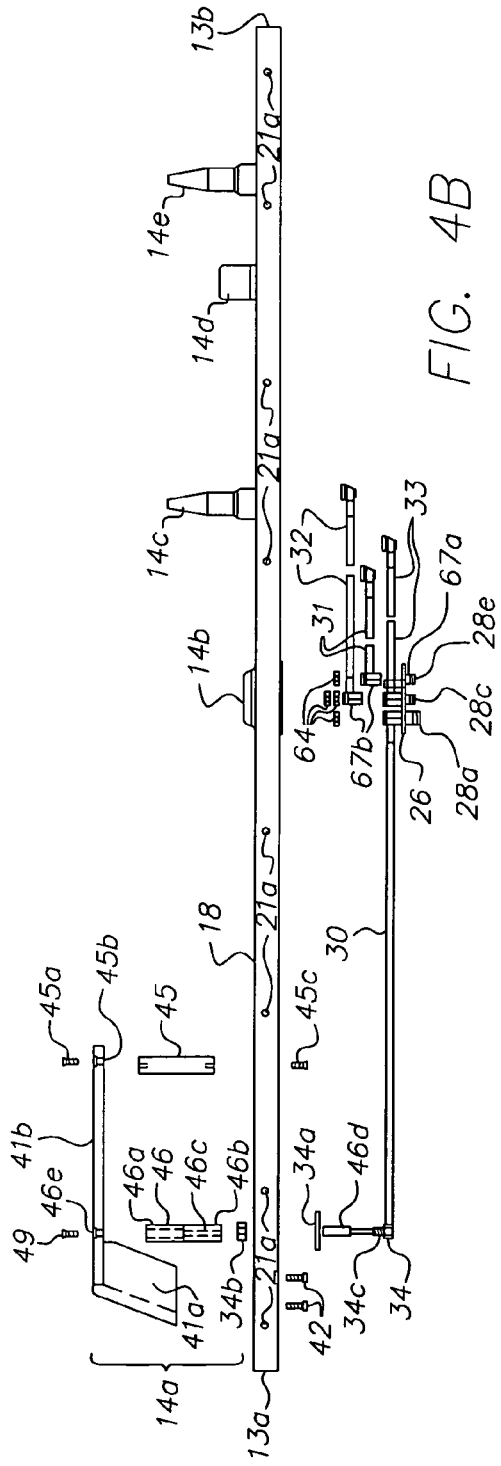
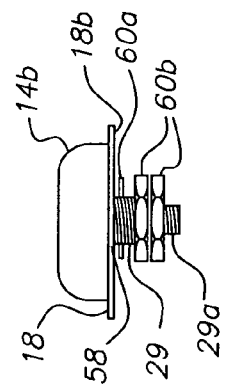
FIG. 4B
FIG. 4C

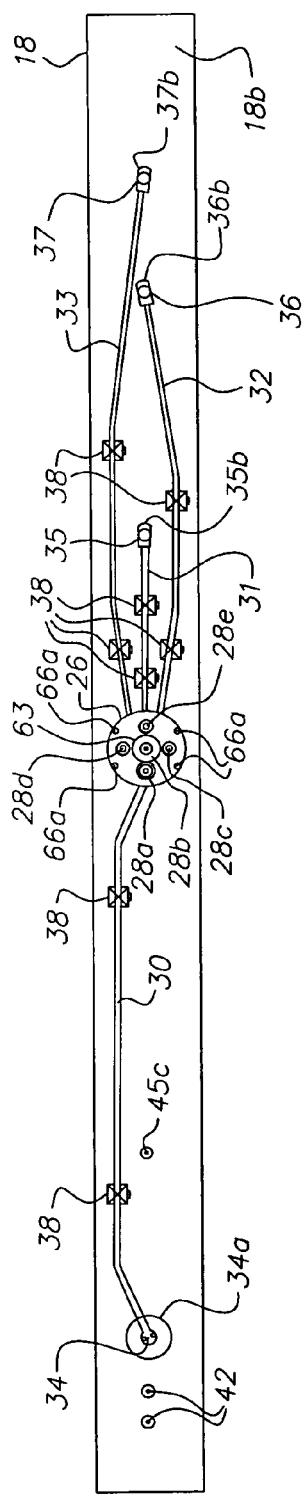
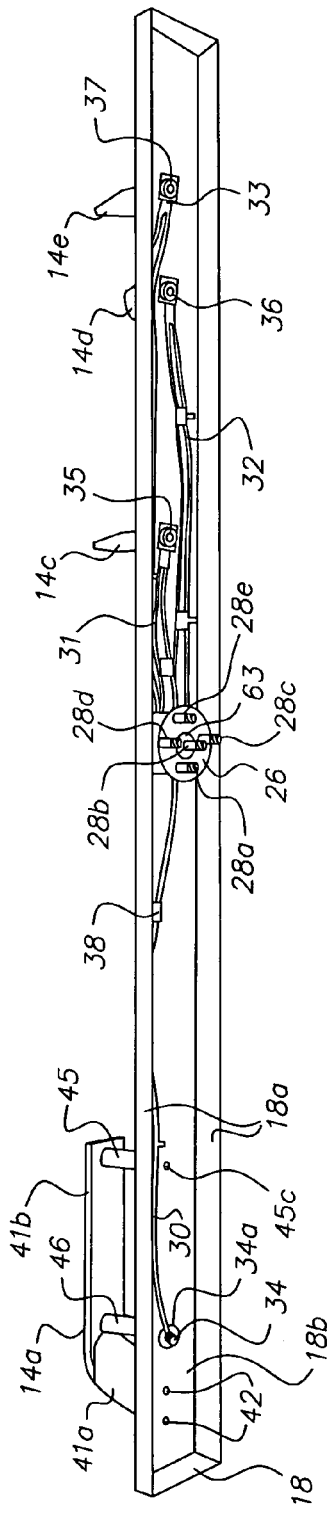
FIG. 5A
FIG. 5B

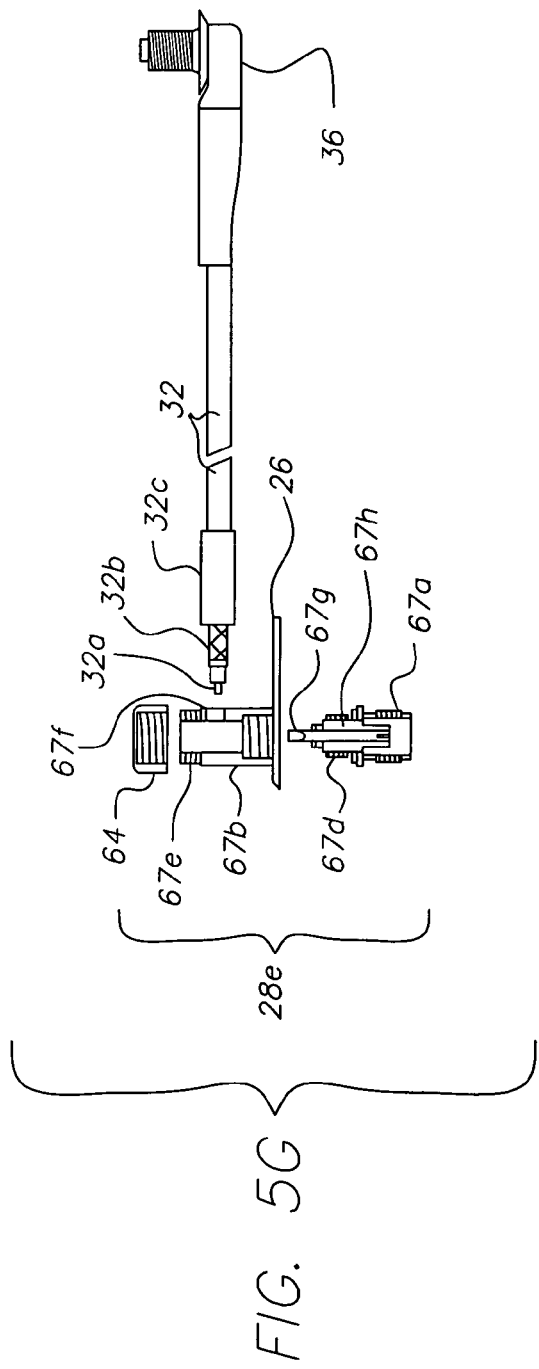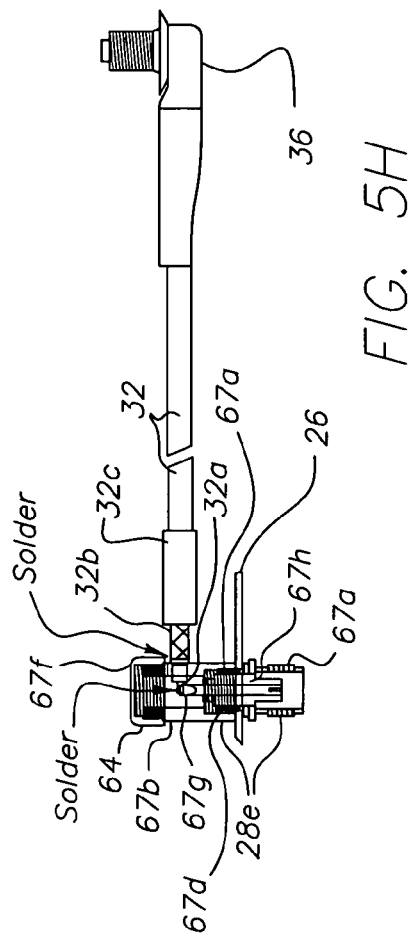
FIG. 5G
FIG. 5H
FIG. 5F

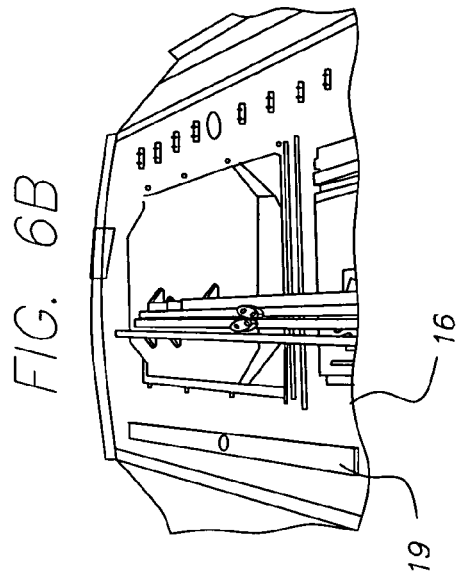
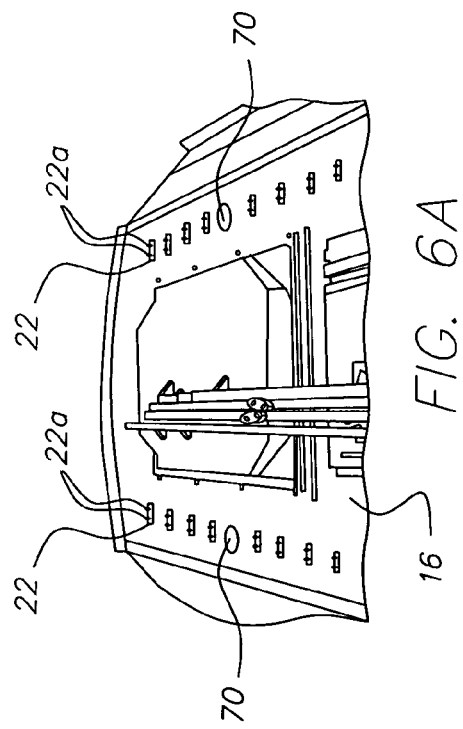
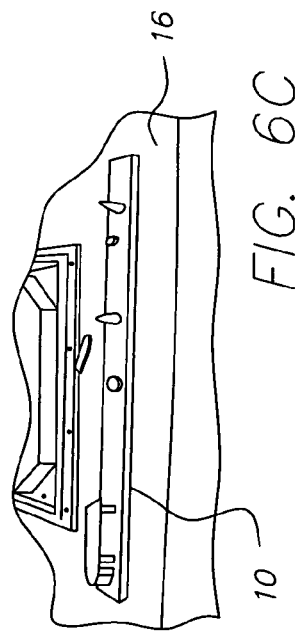

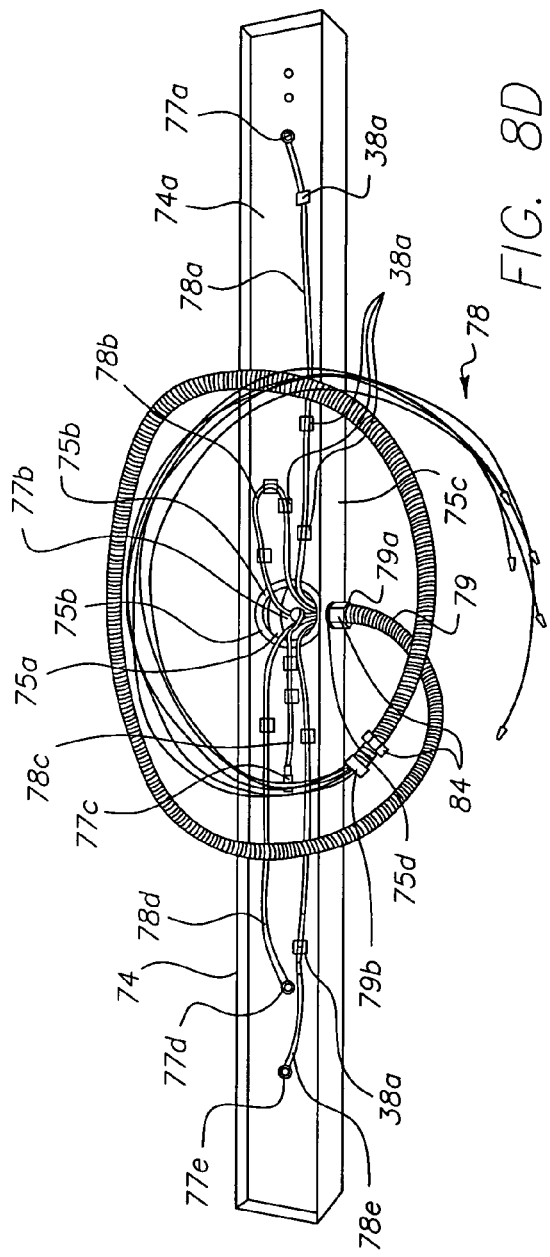
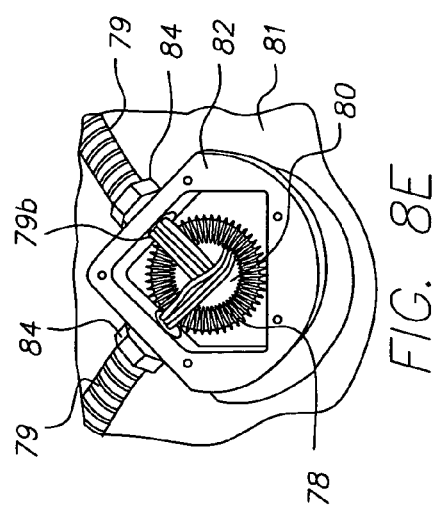

LOCOMOTIVE ANTENNA ARRAYS

FIELD OF THE INVENTION

The present invention relates to locomotives antenna arrays, and in particular to antenna arrays having multiple antenna elements along a housing mountable to the roof of a locomotive, where two or more of the antenna elements are operative at different frequencies or bands to provide a multi-band antenna array. The antenna arrays of the present invention are useful in that they each share a common access hole in the roof of a locomotive for passage of one or more elements (e.g., cables and/or connectors), thereby eliminating the need for multiple roof access holes each for mounting a different antenna element and thus simplifying installation of multiple antenna elements on a locomotive.

BACKGROUND OF THE INVENTION

Today's locomotive is fast becoming a complex communications system incorporating voice, distributed power control, DGPS, digital data links and sensor data communications. The complexity of this environment will continue to increase with the advent of new positive train control systems, and other equipment designed to improve safety and efficiency of the locomotive. Many of these systems have been added to the train over a period of years as different technologies were developed and matured and other new technologies became available. One component common to all of these systems is the antenna. It may be a different size and shape depending on the frequency of operation, but the installation site is always the same.

Typically locomotives in the railroad transportation industry need to be equipped with radio communication systems of different types, GPS, Cellular, PCS, and RF at different communication frequencies (bands). Each communication system needs its own antenna resonant at the desired frequency(s) which is mounted to the roof of the locomotive cab, and then cabling from the antenna feeds through an access hole drilled into the roof to its respective communication system or apparatus. Each antenna needs to be at a suitable location so as not to interfere with each other antenna or cabling of other communication systems. Mounting multiple antennas for different radio system is time-consuming and requires many man hours. For example, mounting just 5 antennas requires at least 5 holes in the roof of the cab for mounting hardware. Further problems often arise when there are multiple antennas to be installed and all of them are targeting the same installation site of the top (or roof) of a locomotive. This is due to the fact that the available ground plane (the top or roof of the locomotive cab) is limited in space, and there are other mechanical systems, such as hand holds, signaling devices, etc. . . . , that need to be there.

Further, there is a need not only to install multiple different antenna systems operating different frequencies or band on new locomotives, but to retrofit existing locomotives that will require these new antenna systems despite the limited space, which can results in a major, very costly overhaul.

It would be desirable to provide an antenna array having multiple antenna elements that is optimized at desired resonant frequencies or bands for locomotive communication systems which can be installed at the same time so as to reduce the cost, time, and labor of installation, and minimizes the number of access holes or opening drilled in the roof of the locomotive. Further is would be desirable to provide such antenna array which can be used both singularly, and in pairs, on the same locomotive, while allowing existing rooftop structures and existing antenna(s), or other system(s) to remain intact.

SUMMARY OF THE INVENTION

It is an object of the present invention to provide an antenna array which overcomes the problems and drawbacks of the prior art.

It is another object of the present invention to provide an antenna array having multiple antenna elements providing communication of signals via a common access hole in the roof of a locomotive when the antenna array is mounted to such roof.

Briefly described, the present invention embodies an antenna array having multiple antenna elements in which two or more of the antenna elements operate at different frequencies or bands, and a housing having a top along which the antenna elements are mounted spaced from each other and a bottom surface mountable onto the roof of a locomotive. Each of the antenna elements has a separate signal path of one or more conductive elements in the housing and shares a common hole along the housing to outside the housing through which the signal path of each antenna element is extendable.

The signal path of each antenna element extends via a common access hole in the roof of the locomotive when mounted thereto for enabling one or more of passage of signals to or from the antenna element. For each antenna element, the conductive elements represent one or more signal carrying parts of connector(s), cable(s), or the like, which can pass signals either from and/or to the resonant material of the antenna element.

The common hole is provided preferably along the bottom or side of the array housing. An access opening or hole in the roof of a locomotive is provided below the array aligned with the common hole when the common hole is along the bottom of the array housing, and elsewhere along the roof when the common hole is along one side of the array housing. Cables can extend from antenna connectors in the housing via the common hole of the array into a roof access opening or hole of the locomotive for connection to communication systems or equipment, or cables from locomotive communication systems may extend upward through the roof access opening or hole to connectors disposed in a plate associated with each of the antenna elements either facing the common hole adjacent, through, or at least partially extending through the common hole.

The antenna elements are preferably mounted along the top of the housing along a dimension extending along the length of the housing, and the location and spacing of the antenna elements along the array is such to provide optimal antenna operation at their respective frequencies or bands.

When the common hole is along the side of the array housing, the housing may have two compartments: an upper housing compartment and an elongated lower housing compartment upon which is stacked the upper housing compartment. The upper housing compartment provides a raised surface for mounting one of the antenna elements (such as a GPS antenna), where the base of the upper compartment has an opening to the lower compartment for passage of a cable from the mounted antenna element on top of the upper compartment. The common hole of the array may then be provided along side of the upper housing compartment through which cables from each of the antenna elements extend for passage into an access hole in the locomotive roof. Such cables may extend from the common hole to such access hole as a bundle through protective tubing.

The housing may be composed of single or multiple compartments having a common hole which preferably is along the bottom or side of the housing, but may be elsewhere along the housing as desired for the particular application, for passage of cables and/or other signal carrying elements associated with the antenna elements mounted to the housing.

Also a diversity antenna system is provided having a pair of antenna arrays each having a multiple antenna elements in which two or more of said antenna elements operate at different frequencies or bands. The antenna arrays are spaced parallel to each other when mounted along a roof of a locomotive.

Although the present invention is described below in connection with locomotives, the antenna arrays may be used on other vehicles for multiband communications.

BRIEF DESCRIPTION OF THE DRAWINGS

The foregoing objects, features and advantages of the invention will become more apparent from a reading of the following description in connection with the accompanying drawings in which:

FIG. 4B is a side view of the upper plate of the antenna array of FIG. 1 during assembly showing the exploded view of the F-type antenna element assembly;

FIG. 4C is a cross-sectional view of the GPS antenna array during mounting on the upper plate of the antenna array of FIG. 1 and prior to assembly with the adapter providing one of the connectors in the connector plate;

FIG. 5A is a bottom view of the upper plate of the antenna array of FIG. 1;

FIG. 5B is bottom perspective view of the antenna array of FIG. 1;

FIG. 5F is a top view of one of caps of FIGS. 4A, 5C and 5D;

FIGS. 5G and 5H are cross sectional views through one of the connectors illustrating its assembly to a cable and to the connector plate, where FIG. 5G is an exploded view and FIG. 5H shows the components assembled;

FIG. 6A is a partial perspective view of the front end of the roof of a locomotive showing the brackets of FIG. 4A during the installation example of a pair of the antenna arrays of FIG. 1 each with an access hole drilled in the roof;

FIG. 6B is the same partial perspective view of FIG. 6A showing of the lower plate of the housing of the antenna array of FIG. 1 attached to the brackets for one of the pair of antenna arrays in which a bottom hole is aligned with the access hole of FIG. 6A;

FIG. 6C is a partial perspective view of the left one of the antenna array installations of FIGS. 6A and 6B arrays showing the same roof of the locomotive of FIGS. 6A and 6B in which the sides of the upper plate of the antenna array housing of FIG. 1 is attached to the sides of lower plate of the antenna array housing of FIG. 6B;

FIG. 8D is a bottom view of the upper plate of the antenna array of FIGS. 8A-8C; and FIG. 8E is a top view of a housing over the access hole in a roof of a locomotive in the case where a pair of arrays of FIGS. 8A-8C in which the cover of the housing is removed.

DETAILED DESCRIPTION OF THE INVENTION

Figure 1:
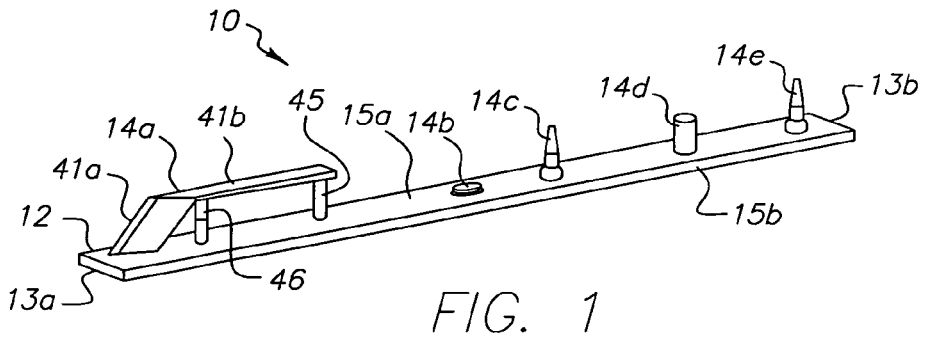
FIG. 1 is a perspective view of the antenna array of the present invention.

Referring to FIG. 1, the antenna array 10 of the present invention is shown having a rectangular housing (or rail) 12 and five antenna elements 14a, 14b, 14c, 14d, and 14e. Each of the antenna elements are mounted other along the top surface 15a of housing 12 spaced from each along a dimension extending along the length of the housing between ends 13a and 13b, and centered about the width of the housing.

Antenna element 14a is a 220 MHZ antenna element which is of a capacitive fed inverted F type, and is dual resonant providing a dual port coupler for two transceivers. Antenna element 14b is an active GPS antenna element having a GPS sensor resonant at 1575 MHz in a radome housing which may be 3 inches in diameter and 0.9 inches in height. Antenna elements 14c and 14e are each a CEL/PCS dual band single port antenna element, such a monopole made from a copper plated element. Antenna element 14d is a 2.4/5.8 GHz dual band single port antenna element of a sleeved dipole single port operative at 2.4 GHz, and having a matched monopole single port operative at 5.8 GHz. Although the above antenna elements are described herein, different types of antenna elements other than those described herein may also be used and mounted upon housing 12. Further, ends 13a and 13b of housing 12 may optionally having mounting plates for right angle VHF or 220 MHz (or both) antenna elements, leaving the main rail along top surface 15a for the higher frequencies and GPS sensor(s). Preferably, the internal elements of the antennas are tuned to their respective bands prior to attachment to housing 12. Further, the highest of antenna elements is elements 14c and 14e which is about 3.75 inches high from the bottom 15b of housing 12, so that the array when mounted on a surface provides a low profile.

Figure 2:
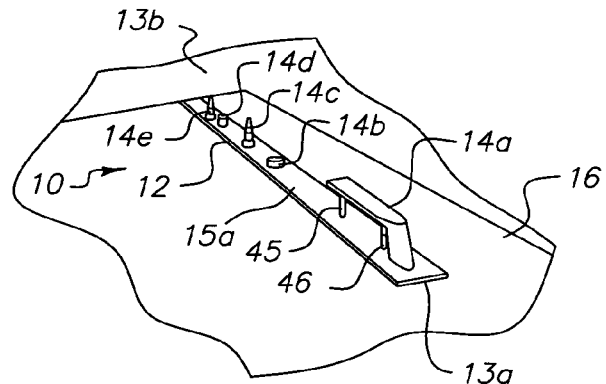
FIG. 2 is another perspective view of the antenna array of FIG. 1 showing an example of the array mounted on the roof of a locomotive.
Figure 3:
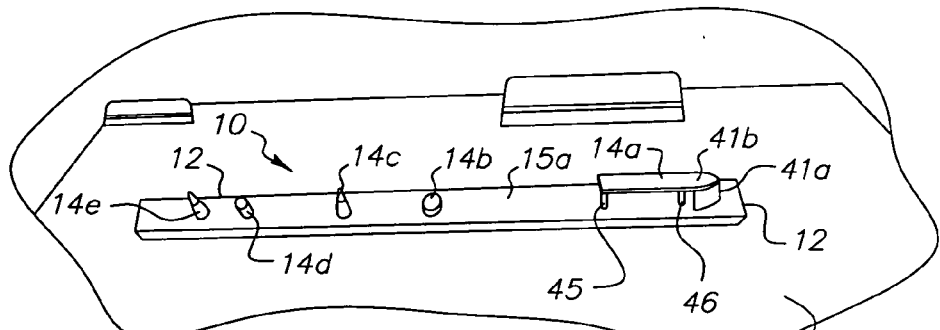
FIG. 3 is another perspective view of the antenna array of FIG. 1 showing an example of the array mounted on the along a slanted part of a roof of a locomotive.

As shown in FIGS. 2 and 3, antenna array 10 is mounted onto the roof or top 16 of a locomotive, such as the locomotive cab section of a train, having communication systems connected by cabling 68 (FIG. 4A) to array 10 to enable operation of such communication systems with the antenna elements 14a-e. FIG. 2 shows the case where bottom surface 15b of antenna array 10 is mounted along a flat (or substantially flat) locomotive roof 16, while FIG. 3 shows the case where the bottom surface 15b of antenna array 10 is mounted along a slanted part of a locomotive roof 16. Any part of the roof of the locomotive may be used so long as such placement is sized for the antenna array, and an access hole drilled in the roof for enables passage of cables 68 to the antenna array 10 with such access hole 70 aligned under a hole 25 in bottom 15b of housing 12. This hole and the access hole are described below in more detail.

Figure 4A:
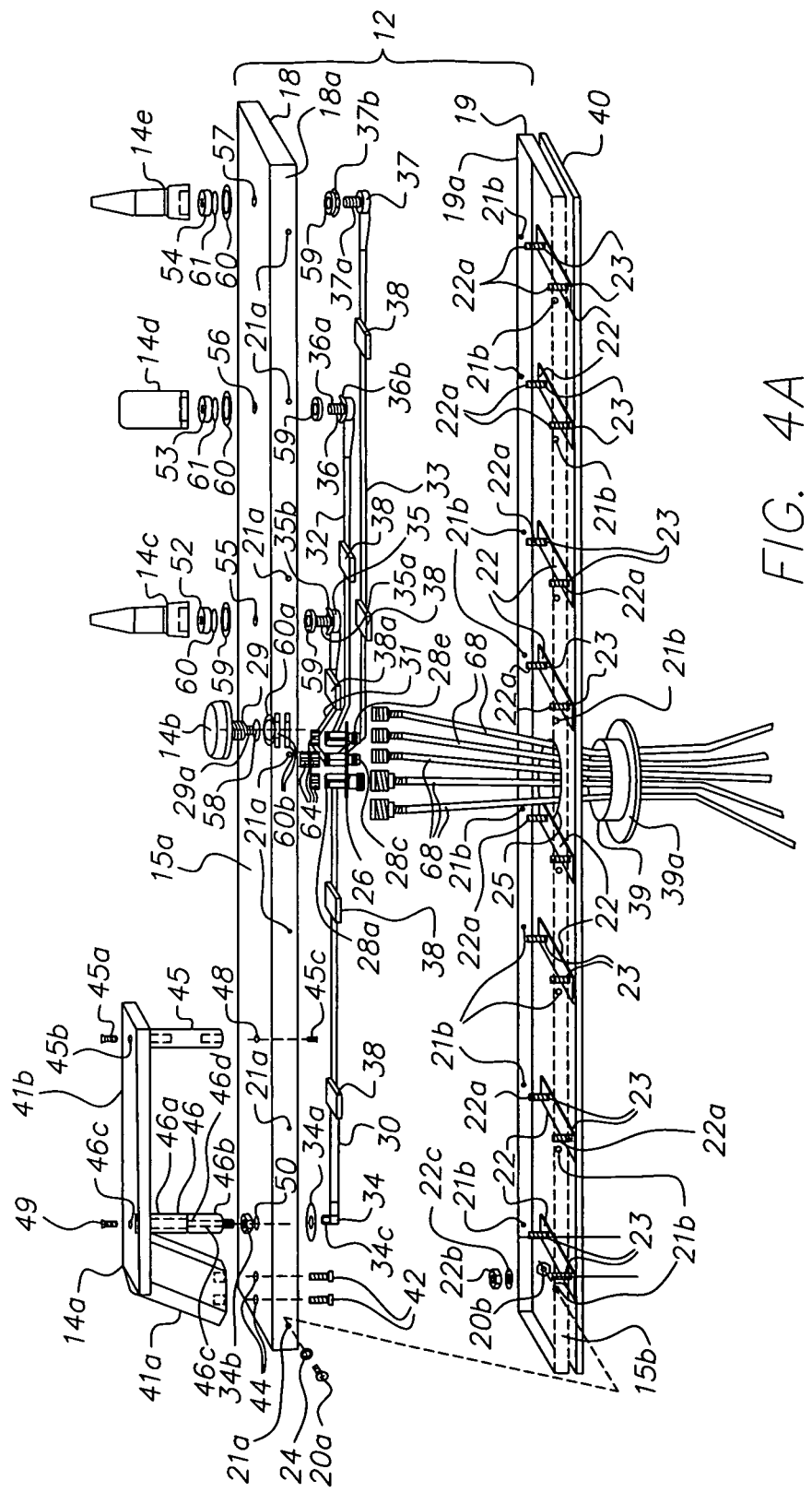
FIG. 4A is an exploded view of the antenna array of FIG. 1.

Housing 12 of antenna array 10 is formed by an upper plate 18 assembly of the mechanical and electrical components of the array, and lower plate 19 which provides mounting of the array to the roof of a locomotive, where the sides of plate 18 cover sides of plate 19 to form a single enlongated compartment therein. FIG. 4A shows the lower plate 19, while FIGS. 1-3 show the upper plate (lower plate 19 not viewable in FIGS. 1-3), while 5A and 5B show the underside of the upper plate 18 by itself prior to being positioned over the lower plate 19.

Preferably, antenna array 10 is mounted along a longitudinal axis of the locomotive as shown in FIGS. 1-3. Although the antenna array 10 is shown mounted with antenna element 14e towards the front of the locomotive and antenna element 14a towards the back of the locomotive, the array 10 may be mounted in the reverse direction, as desired.

Referring to FIG. 4A, an exploded view of the assembly of antenna array 10 is shown. Upper plate 18 and lower plate 19 are attached to each other by screws 20a and self-clinching blind nuts 20b, via washers 24, using sixteen holes 21a and 21b in their sides 18a and 19a, respectively which align with each other when upper plate 18 is properly situated over lower plate 19. For purposes of illustration, only one of screws 20a, self-clinching blind nuts 20b, and washers 24 are shown in FIG. 4A. The upper and lower plates may be made of stainless steel, as well as such screw and nuts connecting them. Hole 25 in lower plate 19 enable access to a connector plate 26 in the housing which faces hole 25 when upper plate 18 is situated over lower plate 19 as described above. The connector plate 26 may extend through (or partly through) hole 25 if desired depending of the distance between plates 18 and 19 and the distance of plate 26 from upper plate 19. Each of the antenna elements 14a-e has a separate signal path of one or more conductive elements in the housing 12 to outside the housing 12 each via a common hole 25 along the housing 12 for enabling one or more of passage of signals to or from the antenna element, as will be described below. Housing 12 may be considered an elongated box. For example, housing 12 may 4 inches in width, 60 inches in length, and 1 inch in height.

Mounting of the housing 12 to a locomotive is enabled by brackets 22 welded to the locomotive roof. Each bracket 22 has two threaded shafts (or studs) 22a. Lower plate 19 has holes 23 through which shafts 22a extend there through. Lower plate 19 attaches to brackets 22 (and thus to locomotive roof) by nuts 22b tightened over shafts 22a via washers 22c. Brackets 22 may each be ¾ inches in width, and made of steel.

Figure 5C:
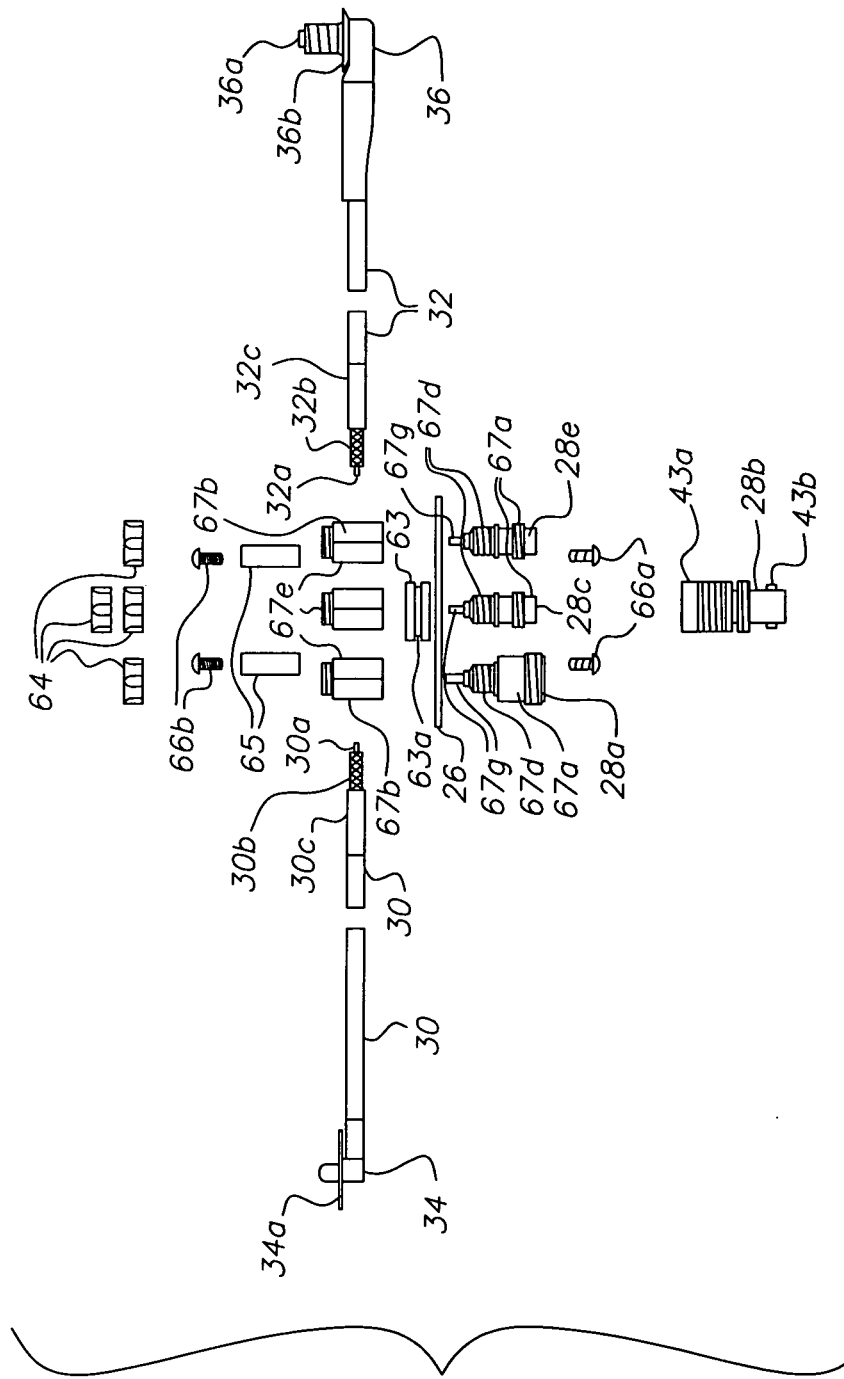
FIG. 5C is an exploded view of the connector plate of FIGS. 4A, 5A, and 5B and showing two of the four feed cables each associated with a different antenna elements of the array.
Figure 5D:
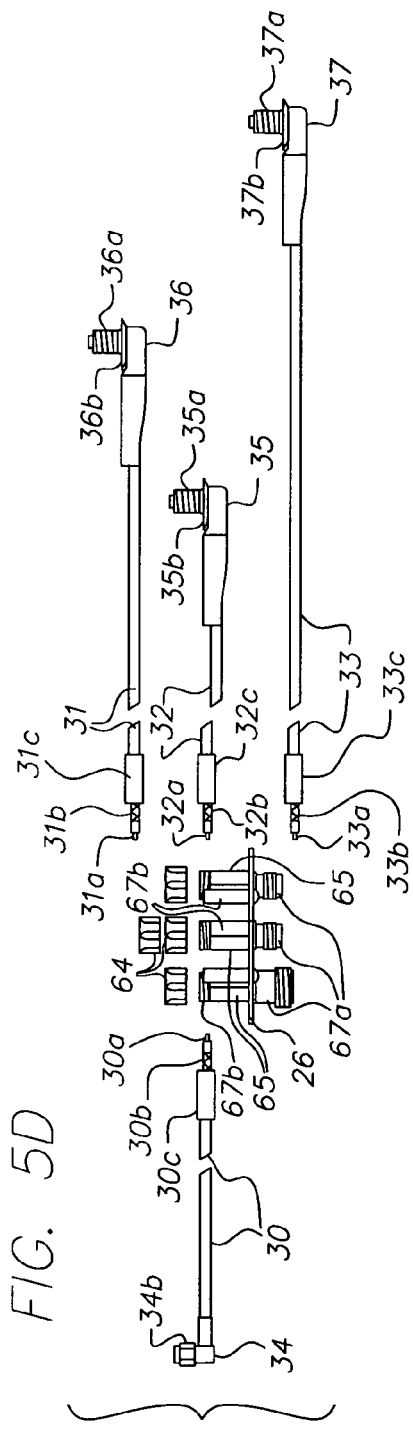
FIG. 5D is a similar to the exploded view of FIG. 5C in which the connector plate is assembled prior to connecting the four feed cables to the connectors fixed in openings of the plate.
Figure 5E:
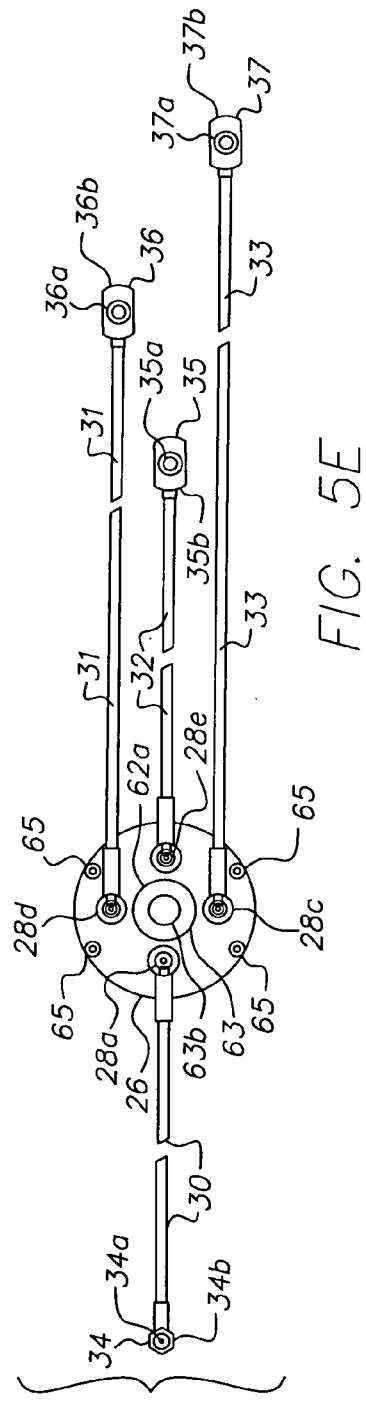
FIG. 5E is a top view of the connector plate of FIG. 5C after connection of the four feed cables without the adapter providing the connector for the GPS antenna element.

Referring to FIGS. 5C-5H, the mechanical and electrical assembly of plate 26, connector 28a-e, and their connections to antenna elements is 14a-e is shown in more detail. Plate 26 may be circular and has a central opening 62a and holes 62b, 62c, 62d, 62e for receiving connectors 28a, c-e. A sealing ring (or grommet) 63, such as of rubber, is received in opening 62a, such that ring is retained in opening 62a by engagement along the ring's outer annular portion 63a, which is of reduced outer diameter from the top and bottom of ring 63 (FIG. 5C). Within ring 63 is an opening 63b (FIG. 5E) into which connector 28b is received. The exterior of connector 28b between ends 43a and 43b frictionally engages ring 63 in opening 63b. For purposes of illustration only connectors 28a, 28c, and 28e are shown in FIG. 4A Connector 28a-e are provided which are mechanically coupled and in a fixed relationship with respect to each other in their respective openings in plate 26. For example, connector 28a is an N-type bulkhead female manufacturer part number RFN-1022-5, and connector 28d is a TNC reverse polarity bulkhead female manufacturer part number RP 1211-1, available from RF Industries of San Diego, Calif. For example, connector 28b is a male TNC to female BNC adapter. Connectors 28c and 28e are each a TNC bulkhead female part number 1220-000-N620-004 available from Simcona Electronics Corp, of Rochester N.Y. Other connectors than these may be used, as desired by the user.

The lower portion 67a of each connector 28a,c-e is of a diameter larger than holes 62b-e, respectively, so that its lower portion 67a lies below plate 26 and its upper portion 67b extends through holes 62b-e, respectively. Connector 28b is positioned in hole 63b of the ring 30 such portion (male TNC) of the adapter extending above plate 26 for attachment to a female TNC connector 29a provided by threaded shaft 29 which extends from GPS antenna element 14b into housing 12 via hole 58. The male TNC of connector 28b has the threads inside the screw nut so that it screws on to the shaft 29 (external threaded) having end 29a. The portion of connector 28b extending below plate 26 provides a female BNC connector for connecting to one of cables 68 having a male BNC male connector. Each of the cables 68 is associated with a different one of antenna elements 14a-e and has the proper male or female connector at their ends for connection to the one connector 28a-e, respectively, as needed for enabling their particular type of connection (e.g., TNC, BNC, or N-type). Connectors 28a-e may be of different types that described above as needed for the locomotive application of array 10.

Standoffs or shafts 65 (FIG. 5C) are provided to retain the position of plate 26 with respect to upper plate 18. The standoffs 65 may be aluminum rods each attached to plate 26 by a screw 66a into a lower threaded end of the standoff, via an hole in plate 26, and the top of each standoff 65 are attached to upper plate 18 by a screw 66b received in an opening in plate 18. For purposes of illustration, standoffs 65 are not provided in FIG. 4A.

Upper portion 67b has a lower threaded interior which is tightened over upper end 67d of the upper portion of each of the connectors 28a,c-e to retain the connector to plate 26 while enabling top of terminal 67g of upper end 67d of upper portion 67b to extend there through, as best shown in the example of the assembly of connector 28e of FIGS. 5G and 5H. Into an opening or side slot 67f of upper portion 67b of each of connectors 28a, 28c, 28d, and 28e is received a stripped end of respective feed co-axial cables 30-33, respectively, opposite their ends having connectors 34-37, respectively. The central wire 30a, 31a, 32a, 33a of stripped end of each cables 30-33, respectively, is soldered (or otherwise electrically and mechanically coupled) to terminal 67g of connectors 28a, 28c-e, respectively, and the shield (e.g., conductive lattice) 30b, 31b, 32b, 33b of each of cables 30-33 is soldered (or otherwise electrically and mechanically coupled) to upper portion 67b. Once soldered, shrink wrap tubing 30c, 31c, 32c, 33c is applied and heated to provide a water proof seal about opening 67f of upper portions 67a of connectors 28a, 28c-e, respectively. This is shown for example in FIG. 5H prior to placement of shrink wrap tubing. To enable proper grounding, the exterior of the upper and lower portions 67a and 67b are conductive, such as of brass or other conductive metal and thus are in electrical contact with shield 30b, 31b, 32, and 33b, and electrically separated (not connected) to terminal or metal pin 67g by an insulator member 67h supporting terminal 67g in lower end 67a. Arrows in FIG. 5H indicate areas where soldering is carried out Upper portion 67b has an externally threaded end 67e upon which is tightened an internally threaded cap 64. Cap 64 may have open ends as shown in FIG. 5F, or the cap 64 for connectors 28a, 28c-e, may have a closed top end.

Prior to situating upper plate 18 over lower plate 19, the antenna elements 14a-e are mounted to the top surface 15a of upper plate 18, using their respective connectors 34-37 to co-axial cables 30-33, respectively 28a, c-e. Although plate 26 is preferred, array 10 may be provided without connector plate 26 in which cables 68 are either coupled to connectors 28a-e, or directly to connectors 34-37 without connectors 28a-e.

As shown in FIGS. 4A and 4B, antenna element 14a has a vertical member 41a and a horizontal member 41b which may be molded together, such as of aluminum, in which the antenna resonant material is provided in horizontal element 41b. Vertical member 41a is slanted towards end 13a of housing 12 and fixed to upper plate 18 by two screws 42 each received in threaded holes of vertical member 41a via holes 44 of upper plate 18. In addition to member 41a, two cylindrical members 45 and 46 are provided to support horizontal member 41b at a position above and parallel to upper plate 18.

One end of member 45 is attached to horizontal member 41b by a screw 45a into hole 45b in horizontal member 41b. The other end of support member 45 is attached by a screw 45c in a threaded hole of support member 45 via a hole 48 in upper plate 18. To electrically connect horizontal member 41b to connector 34, member 46 is composed of two cylindrical stacked portions 46a and 46b having an internal bore 46c shaped to receive rod 46d. Rod 46d extends through member 46, as shown in dashed lines. A metal screw 49 is a tighten through a hole 46e in horizontal member 41b into a threaded hole at one end of rod 46d. The other end of rod 46d extends through nut 46c above plate 18, hole 50 in upper plate 18, through a circular metal ring 34a below plate 18 and is then received in the center of connector 34 which extends upward through hole 50, and then is retained by nut 34b tightened about the outer thread 34c of connector 34. The conductive material of rod 46a is thus electrically connected to wire 30a extending through cable 30 to pass antenna signals there through. For grounding, ring 34a provides electrical contact about the exterior surface of connector 34 to upper plate 18, such that ring 34a electrically connects plate 18 to the shield 30b (FIG. 5) that extends through cable 30. For example, connector 34 may be a commercially available connector SMA right angle crimp RF Industries part number RSA-3010-C.

Antenna element 14b is mounted to upper plate 18 as best shown in FIG. 4C in which threaded shaft 29 extends through hole 58 in upper plate 18, such that the back surface of the radome lies against the top surface of upper plate 18. Then under plate 18 a washer 60a is positioned over shaft 29, and then mounting and locking nuts 60b are tightened over shaft 29 which is threaded to receive such nuts 60b. FIG. 4C shows placement of washer 60a and nuts 60b prior to tightening the nuts to lock the antenna 14b to upper plate 18. Shaft 29 having end 29a screws into an upper end 43a of connector 28b (FIG. 5C). In other words, the female TNC connector provided by threaded shaft 29 is attached to a portion (male TNC) of connector 28b above plate 26.

Antenna element 14b is grounded through its metal base mounting stud provided by the upper part of shaft 29 that has the external threads. The metal base extends through the plate 18 and is tightened against upper plate 18, via washer 60, by the two nuts 60b, thereby providing the metal to metal contact required for the grounding. The female TNC connector provided by shaft 29 is connected to the male TNC of connector 28b, as typical of TNC coupling to pass antenna signals there through and provide a ground connection. Plate 26 is centrally located below antenna element 14b enabling connector 28b to be retained in ring 63. Alternatively antenna element 14b may have a feed cable and connector as similarly used with other antenna elements 14a, b-e.

Antenna elements 14c, 14d and 14e each has an opening about its lower end with a threaded interior for receiving circular threaded nuts 52, 53, and 54, respectively. Connector 35, 36, and 37 each has a threaded end as shown in FIG. 4A, which extends through holes 55, 56, and 57, respectively, of upper plate 18, via a washer 59, and after passing through their respective hole then passes through an O-ring 60, another washer 61, and is received and tightened in the threaded interior of nuts 52, 53, and 54, respectively. Each O-ring 60 provides for a weather tight seal between the antenna elements 14c-e and surface 15a of upper plate 18. The central wire for each of the cables 30-33 extends through the cable and then electrical connects to the central upright (or right angle) members 35a, 36a, and 37a, respectively, of connectors 35, 36, and 37, respectively, for passing signals from their respective antenna elements. For grounding, the shield 31b, 32b, 33b of cables 31-33, respectively, extends through the respective cable and then is electrical connected to flanges 35b, 36b, 37b, respectively, which abut surface 18b of upper plate 18 when their respective antenna elements are attached to connectors 35, 36, and 37. For example, connectors 35-37 may each be commercially available components from Whisco Component engineering part number A1002A. Preferably, the means for mounting antenna elements 14c-e to upper plate 18 are each the same, but different means may be used. Plastic adhesive cable tie mounts 38 (FIGS. 4A, 5A, and 5B) may be spaced along cables 31, 32, 33 (as well as for cable 30) to retain such cables along the interior top wall 18b of housing 12, i.e., the underside of upper plate 18.

Thus, each of antenna elements 14a, 14b, 14c, 14d, and 14e has a separate signal path of one or more conductive elements. For antenna element 14a, such one or more conductive elements (e.g., wire 30a of cable 30, rod 46d, and signal carrying part of connector 28a provided by pin 67g extending there through) connect resonant material of antenna element 14a to connector 28a and to one of cables 68. For antenna element 14b, such one or more conductive elements (e.g., shaft 29 and the signal carrying part of connector 28b) connect the resonant material of the antenna element to connector 28b and to a different one of cables 68. For antenna elements 14c, 14d, and 14e, such one or more conductive elements (e.g., wires 31a, 32a, 33a of cables 31, 32, and 33, respectively, connector members 35a, 36a, 37a, respectively, and the signal carrying part of connectors 28c, 28d, and 28e, respectively, provided by pin 67g extending there through) connect the resonant material of the respective antenna element to connectors, 28c, 28d, and 28e, respectively, to other different ones of cables 68.

Hole 25 in bottom 15b of housing 12 is sufficient in size for passage of at least five cables 68 each for attachment to a different one connector's 28a-e, via an access hole or opening 70 below antenna array 10 preferably drilled prior to installation of the antenna array, as for example shown in FIG. 6A prior to attachment of lower plate 19 to brackets 22 shown welded to the locomotive roof 16. The access hole 70 is drilled in a location in which cables 68 can pass within the locomotive to their particular communication systems. A flange 39 (FIG. 4A) slightly less that the diameter of hole 25 extends through the access hole 70. Flange 39 has a annular lip 39a welded (or otherwise attached) along the interior of the locomotive about access hole 70. Flange 39 may be made of steel or other conductive material. Preferably, a layer of foam material 40 is provided along the bottom surface 15*b* prior to attachment of lower plate 19 to brackets 22. Holes are provided in the foam material for extending shafts 22*a*, and flange 33.

FIG. 6B then shows the attachment of lower plate 19 to brackets 22 in which hole 25 is the same or substantially the same in diameter and positioned in alignment over the access hole 70, with flange 39 now extending through hole 25. Thus, flange 39 extends through hole 25 along the edges thereof after passing and being attached to roof 16. FIG. 6C shows the finished assembly of upper member 18 positioned over lower plate 19 and attached thereto.

Although one of the arrays 10 may be used on a locomotive, or any other vehicle needing multiband antenna operation, preferably two of arrays 10 are utilized as part of a diversity antenna system. For example, a pair of arrays 10 are attached to roof 16 of a locomotive 66 in FIG. 7. The arrays are spaced parallel to each other and in reverse orientation so that antenna element 14*a* of each of the arrays spaced farther apart from each other to minimize interference than if both arrays were disposed along the same direction (e.g., diagonally across from each other). Less preferably, each array 10 of the pair may be oriented with their common antenna elements 14*a-e* facing the same direction (e.g., common antenna elements of each array 10 across from each other). Each of the arrays has a separate access hole 70 in roof 16 for installation of the array through which their respective cables 68 are passed and coupled to the array for connection to communication systems in the locomotive. FIGS. 6A-6B show part of the installation of the arrays on locomotive 72. Preferably, the pair of arrays are longitudinally oriented with respect to the length of the of locomotive, but may instead be oriented along other dimensions (such as width of locomotive) or non-parallel with each other. Further, although two antenna arrays are shown, one or any number of arrays may be used as desired for the particular application, in which cables of common type antenna elements from multiple ones of arrays 10 provide signals to common or different communication systems in the locomotive.

Figure 8A:
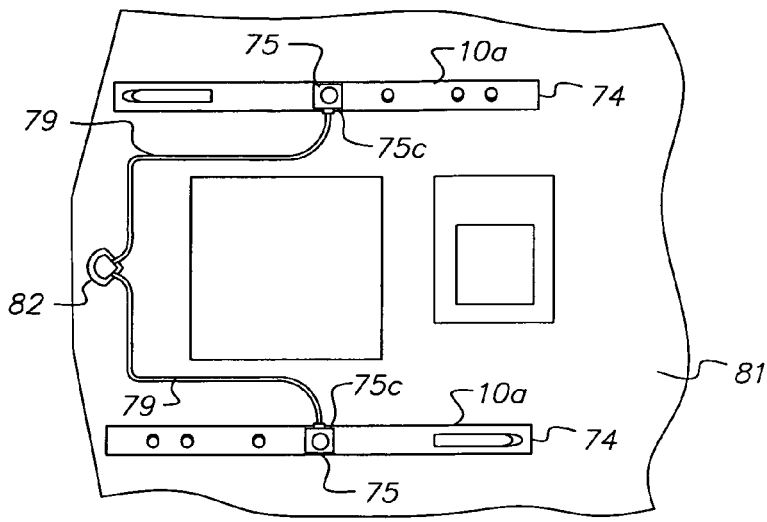
FIGS. 8A, 8B, and 8C show another embodiment of the antenna array of the present invention with and without a cover, and use of a pair of such arrays.

Referring to FIGS. 8A-8E, an antenna array 10*a* of another embodiment of the present invention is shown for a locomotive or any other vehicle needing multiband antenna operation. Antenna array 10*a* has a housing 12*a* with multiple mounted antenna elements 76*a*, 76*b*, 76*c*, 76*d*, and 76*e*. Housing 12*a* has a lower plate which is the same as lower plate 19 of array 10 but without hole 25, and an upper plate 74, which may be of the same size, material, and shape as upper plate 18. Housing 12*a* has two compartments. The first lower compartment being defined by upper and lower plates and their respective sides. The second upper compartment is formed by a structure of walls which extend from upper plate 74 of housing 12*a* to a top wall parallel to upper plate 74 upon which antenna element 76*b* is mounted. This box like structure provides an extension 75 of housing 12*a*. The bottom of this structure may have a base or bottom wall which is attached, such as by screws and nuts, to upper plate 74, through aligned holes in the base and upper plate 74. As best shown in FIG. 8D, the base of housing extension 75 has an opening 75*b* aligned with an opening 74*b* of upper plate 74, such that compartment of housing 12*a* extends upwards into the compartment of its extension 75. Section 75 may be made of the same material as upper plate 74.

Antenna element 76*a* is of the same type as antenna element 14*a* and is similarly mounted via a hole in upper plate 74 as described above to upper plate 18. Antenna element 76*b* may be of the same type as antenna element 14*b*, and is mounted to via a hole in housing extension 75 in the same manner as element 14*b* is mounted to upper plate 18. Antenna element 76*c-e* may be of the same type as antenna elements 14*c-e* and each is mounted via a hole in upper plate 74 as described above to upper plate 18.

Connectors 77*a-e* are provided for antenna elements 76*a-e*, respectively, in housing 12*a*. Connectors 77*a-e* are each connected to a cable 78*a-e*, respectively, which are feed as a bundle 78, via a hole (or opening) 75*d* in side wall 75*c* of housing extension 75, into a tubing 79 (e.g., flexible plastic or bent metal tube) having one end 79*a* attached to hole 75*d*. Plastic adhesive cable tie mounts 38*a* may be spaced along each cable 78*a-e* to retain such cable along the interior top wall 74*a* of housing 12*a*, i.e., the underside of upper plate 74. Cable 78*b* extends from connector 77*b* located along surface 75*a* of housing extension 75 and is mounted by mounts 38*a* to wall 74*a* prior to reentering back into the housing extension via opening 74*b* and hole 75*b* for exiting through opening 75*d* into tubing 79. Thus, each of the antenna elements 76*a*, 76*b*, 76*c*, 76*d*, and 76*e* has a separate signal path of one or more conductive elements (e.g. cables 78*a*, 78*b*, 78*c*, 78*d*, and 78*e* in the housing 12*a* to outside the housing 12*a* each via a common hole 75*d* along the housing 12 for enabling one or more of passage of signals to or from the antenna element to communication systems in the locomotive.

Tubing 79 and bundle 78 each being of a length to enable bending along the roof (such as around other roof component(s) which may be present) as needed to a desired location for a roof access hole to pass cables of the bundle into a locomotive. Such tubing 79 is shown disconnected in FIG. 8D at its end 79*b* with bundle 78 extending there through, prior to placement the cables of the bundle from such end 79*b* into an access hole in the roof of a locomotive.

Figure 8B:
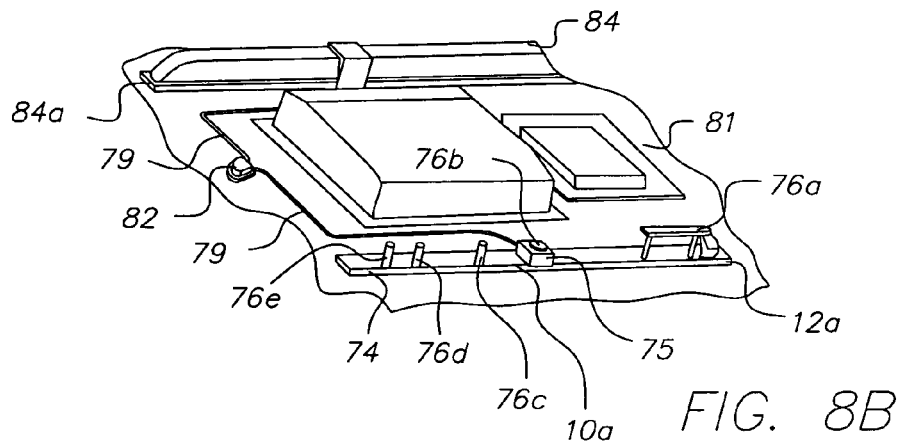
Figure 8C:
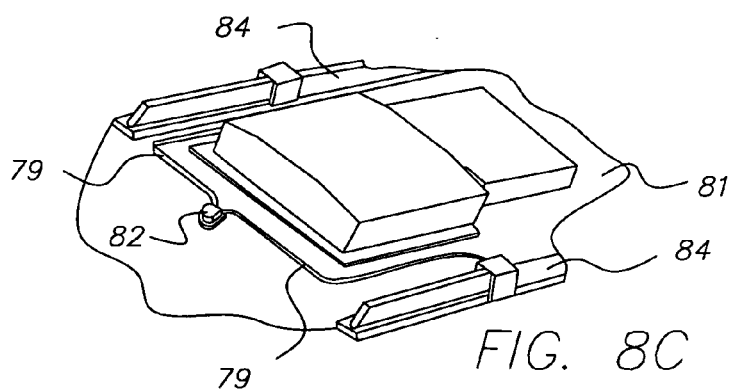

A pair of array 10*a* is shown mounted to roof 81 of a locomotive in FIGS. 8A-8C. Each of the two arrays 10*a* has a separate tubing 79 coupled to the array at one end 79*a* and then extending along roof 81 at the other end 79*b* into an opening of a housing 82 which covers an access hole 80 drilled in roof 81. Thus two bundles 78 are received in hole 80, one from each array 10*a*. Housing 82 may be welded to roof 81 or attached by other mechanical means, such nuts and bolts. A cover of housing 82 is removed in FIG. 8E showing the exiting of cables 78*a-e* from the tubing 79 associated with each of the arrays 10*a* into hole 80. Tubing end 79*a* and end 79*b* are screwed into housing 75 and 82, respectively, about threads along the interior of their respective opening or hole of housing 75 and 82, respectively, and then retained by a nut 84 tightened over threaded end 79*a* and 79*b*. For example, nut 84 is shown removed from end 79*b* in FIG. 8D prior to attachment of tubing 79 into the opening or hole for such tubing in housing 82, and then attached to housing 82 in FIG. 8E by nut 84. Tubing 79 may be mounted to roof 81 between each of the arrays 10*a* and the housing 82.

Each of the pair of arrays 10*a* may have a cover 84, such as plastic. The same hardware used to attach upper and lower plates together in array 10 is used in array 10*a* (e.g., screws 20*a*, self-clinching blind nuts 20*b*, and washers 24), and when cover 84 is present such hardware is also used to attach the base 84*a* of cover 84 to housing 12*a* of array 10*a*. The tubing 79 for each array 10*a* is fed through a hole in cover 84. A cover may similarly be provided over array 10, if desired, but without a portion for accommodating extending housing 75 and tubing 79.

Figure 7:
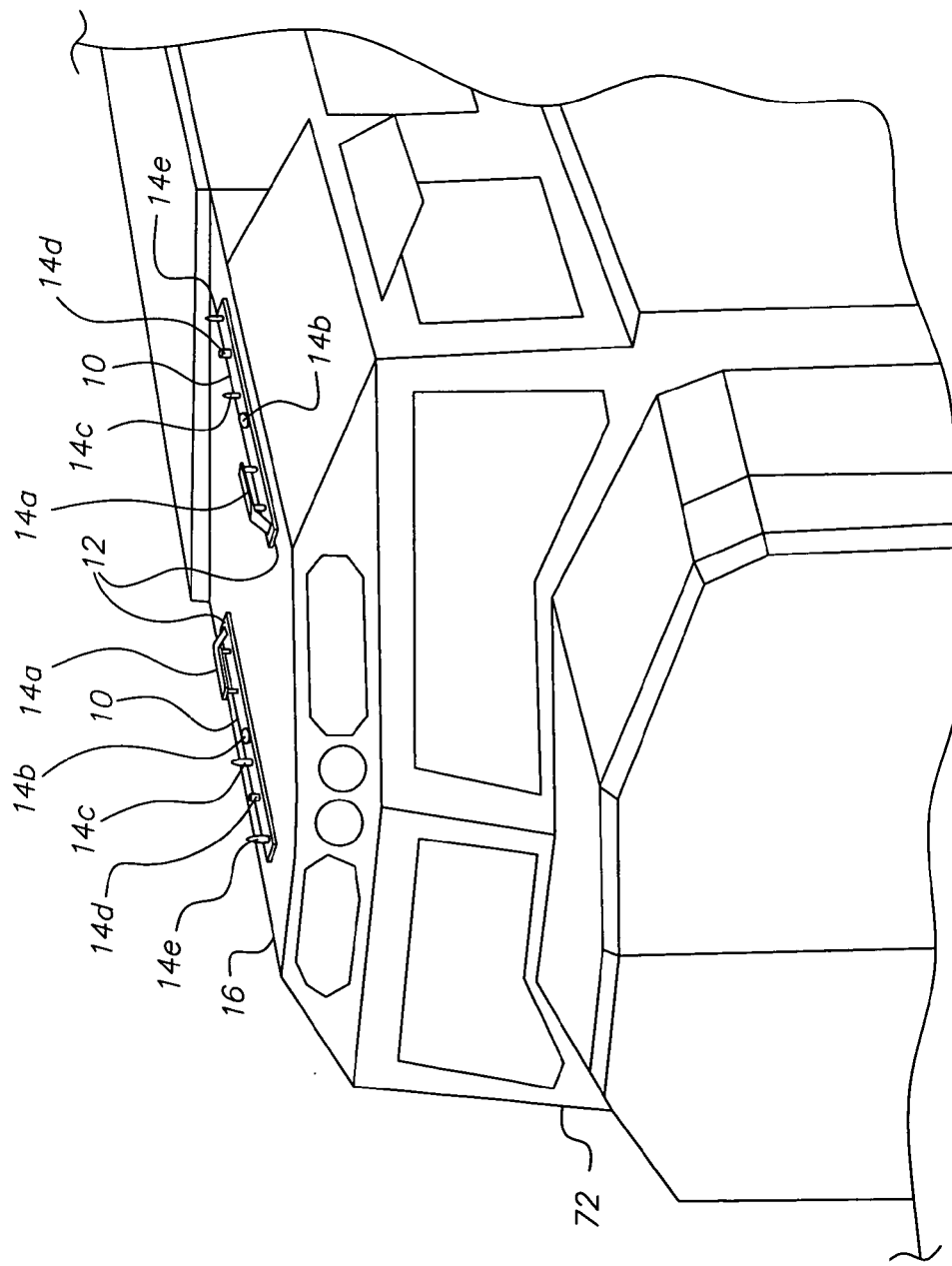
FIG. 7 shows a partial perceptive view of a locomotive cab with a pair of antenna arrays of FIG. 1.

Although occupying more of the ground plane of the locomotive, one advantage of array 10*a* is that only one access hole in the roof is needed for a pair of arrays which may be desired for a particular application, rather then the pair of arrays 10 as shown in FIG. 7 which has two access holes in the roof one for each array 10. Although a pair of arrays is shown, a single one of the arrays 10a may be used. In the case of mounting a single array 10a, the access hole in the roof may be beside array 10a (or spaced a different distance from that shown in FIGS. 8A-C), and tubing 79 length adjusted accordingly. Both array 10 and 10a can be used singularly, or in pairs on the same locomotive with the same or a different set of antenna elements, and further arrays 10 and 10a can be placed on a roof of a locomotive while allowing other rooftop structures, such as existing antenna elements mounted to the roof (or other roof top devices which limit the available ground plane), to remain intact.

The five antenna elements 14a-e (or 76a-e) are believed to be positioned in the figures for optimal (or best performance possible) with respect to each other within array 10 (or 10a). In other words prior to installation of the array onto a locomotive, the antenna arrays are pre-optimized for their best performance (in terms of location and spacing from each other) along the array so that optimal antenna operation is obtained at their respective frequencies or bands. This provides an advantage over the prior art in which each antenna element requires individual roof mounting and one must account for any other antennas already roof mounted effects along the limited roof space to avoid interference or other deleterious. Other positions may also be used depending on the particular application, and thus the antenna array is configurable by placing all or some of elements 14a-e (or 76a-e) in different locations on along the housing. Further, although five antenna elements are shown in the figures, any number less than five, or more than five, may be used at different positions, where housing 12 (or 12a) is sized appropriately to accommodate the antenna elements and the desired spacing from each other, and also the connectors on plate 26 if the case of array 10 are provided for at least the proper number of antenna elements with one or more conductive elements being provided between each connector and their respective antenna element. The particular antenna elements 14a-e shown in the figures are manufactured by Sti-co Industries, Inc., of Orchard Park, N.Y., but antenna elements of other manufactures may also be used of the same or different frequency bands with their associated mounting mechanism to housing 12 (or 12a).

Although preferably connector plate 26 or other member stationary with respect to upper plate 18 is provided in array 10, when connector plate 26 is not provided, cables (or combination of coupled cables by connectors) provide a signal carrying path for each of antenna elements 14a-e to outside the housing via hole 25. Alternatively, hole 25 may represent or be replaced by one of multiple holes in housing 12 to outside the housing for passage of at least one cable extended through each of the holes leading to an access hole in the roof of the locomotive, where each cable is connected to, or is a part of, one or more conductive elements of a different one of the antenna elements. Similarly, hole 67g in upper housing compartment 75 may represent or be replaced by one of multiple holes along the side of housing 12a, with or without upper compartment 75, to outside the housing for passage of one cable or a subset of cables from the antenna elements to a single access hole in a locomotive roof.

From the foregoing description, it will be apparent that antenna arrays and systems using same has been provided. Variations and modifications of the herein described antenna array will undoubtedly suggest themselves to those skilled in the art. Accordingly, the foregoing description should be taken as illustrative and not in a limiting sense.

The invention claimed is:

1. An antenna array comprising:
   a plurality of antenna elements in which two or more of said antenna elements operate at different frequency bands;
   a housing along which said plurality of antenna elements are mounted, and said housing is mountable onto a roof of a locomotive; and
   each of said antenna elements has a separate signal path of one or more conductive elements in said housing and shares a common hole along said housing to outside said housing through which the signal path of each antenna element is extendable, wherein the signal path of each of said antenna elements extends via a common access opening in the roof of the locomotive when said housing is mounted onto the roof of the locomotive, and a connector associated with each of said antenna elements is disposed in a different opening of a plate fixed to said housing for enabling access from outside said housing to the signal path of each of said antenna elements via said connector, in which said plate is one of within said housing facing said common hole or at least partially extends through said common hole.

2. The antenna array according to claim 1 wherein said housing has a top surface having a hole for each of said antenna elements in which the antenna element is mounted to a different connector under said antenna element in said housing which provides one of said one or more conductive elements associated with antenna element.

3. The antenna array according to claim 1 wherein said one or more conductive elements for each of said antenna elements further comprises at least a cable.

4. The antenna array according to claim 1 wherein said antenna elements are mounted along said housing spaced from each other along a dimension extending along the length of said housing.

5. The antenna array according to claim 4 wherein two of said antenna arrays are mountable onto the rooftop of the locomotive parallel to each other along their respective lengths.

6. The antenna array according to claim 1 wherein said housing has a top surface and a bottom surface and said common hole extends through said bottom surface of said housing.

7. The antenna array according to claim 1 wherein said housing has a top surface provided by an upper plate and, and bottom surface provided by a bottom plate for mounting said housing onto the locomotive.

8. The antenna array according to claim 1 wherein said antenna elements are selected from a group consisting of CEL/PCS antenna element, a 2.4/5.8 GHz antenna element, GPS antenna element, and a 220 MHz antenna element.

9. The antenna array according to claim 1 wherein said common hole extends through a bottom of said housing, and one of said antenna elements is mounted onto said housing above said common hole, and said one or more conductive elements for said one of said antenna elements is provided by the connector associated with said one of said antenna elements, and said one or more conductive elements for other of said antenna elements further comprises at least a cable.

10. The antenna array according to claim 1 further comprising a plurality of brackets attachable to the rooftop of the locomotive for mounting said housing along the bottom thereof.

11. The antenna array according to claim 1 wherein said housing is mountable onto the surface of the rooftop of the locomotive without impacting any other structure on the rooftop.

12. The antenna array according to claim 1 further comprising a cover upon said housing which extends over said antenna elements.

13. The antenna array according to claim 1 in which at least two of the connectors associated with different ones of said antenna elements represents different types of connectors.

14. The antenna array according to claim 1 wherein said common hole extends through a bottom of said housing, said connector for each of said antenna elements is connectable to a cable via said common access opening in the roof of the locomotive which aligns with said common hole when said housing is mounted onto the roof of the locomotive.

15. An antenna array for a locomotive comprising:
a plurality of antenna elements in which two or more of said antenna elements operate at different frequency bands;
a housing along which said plurality of antenna elements are mounted, and said housing is mountable upon a rooftop of a locomotive uncombined with any non-antenna related raised structure mounted upon said rooftop; and
each of said antenna elements has a separate signal path of one or more conductive elements in said housing and shares a common hole along said housing to outside said housing through which the signal path of each antenna element is extendable, wherein said housing further comprises an upper compartment and a lower compartment, in which said common hole is provided along a side of said upper compartment.

16. The antenna array according to claim 15 wherein the signal path of each of said antenna elements extends outside said housing via an access hole in the rooftop of the locomotive when said housing is mounted onto the rooftop of the locomotive.

17. The antenna array according to claim 16 wherein said signal path of one or more conductive elements for each of said antenna elements has at least a cable which is extendable through said common hole to said access hole when said housing is mounted onto the rooftop of the locomotive.

18. The antenna array according to claim 15 wherein said upper compartment is disposed over said lower compartment with an opening between said upper compartment and said lower compartment, said lower compartment is elongated to extend along a length of said housing, said upper compartment has a top surface with one of said antenna elements, and said lower compartment has a top surface with other of said antenna elements.

* * * * *